US00RE44501E

(19) United States
(12) Reissued Patent
Janna et al.

(10) Patent Number: US RE44,501 E
(45) Date of Reissued Patent: Sep. 17, 2013

(54) HINDFOOT NAIL

(75) Inventors: Sied W. Janna, Memphis, TN (US); William Stewart, Memphis, TN (US); Roy W. Sanders, Tampa, FL (US)

(73) Assignee: Smith & Nephew, Inc., Memphis, TN (US)

(21) Appl. No.: 12/855,377

(22) Filed: Aug. 12, 2010

Related U.S. Patent Documents

Reissue of:
(64) Patent No.: 7,410,488
Issued: Aug. 12, 2008
Appl. No.: 11/061,699
Filed: Feb. 18, 2005

(51) Int. Cl.
*A61B 17/58* (2006.01)

(52) U.S. Cl.
USPC ..... 606/62

(58) Field of Classification Search
USPC ..... 606/62–68; 623/21.18
See application file for complete search history.

(56) References Cited

U.S. PATENT DOCUMENTS

| | | | |
|---|---|---|---|
| 2,136,471 | A | 11/1938 | Schneider |
| 2,952,254 | A | 9/1960 | Keating |
| 2,987,062 | A | 6/1961 | Ellison |
| 3,272,204 | A | 9/1966 | Artandi et al. |
| 3,463,158 | A | 8/1969 | Schmitt et al. |
| 3,531,561 | A | 9/1970 | Trehu |
| 3,596,656 | A | 8/1971 | Kaute |
| 3,636,956 | A | 1/1972 | Schneider |
| 3,739,773 | A | 6/1973 | Schmitt et al. |
| 3,876,068 | A | 4/1975 | Sonnino |
| 3,892,649 | A | 7/1975 | Phillips et al. |
| 3,902,497 | A | 9/1975 | Casey |
| 3,918,100 | A | 11/1975 | Shaw et al. |
| 3,937,223 | A | 2/1976 | Roth |
| 3,960,151 | A | 6/1976 | Kuhn |
| 4,135,507 | A | 1/1979 | Harris |
| 4,146,936 | A | 4/1979 | Aoyagi et al. |
| 4,186,448 | A | 2/1980 | Brekke |

(Continued)

FOREIGN PATENT DOCUMENTS

| | | |
|---|---|---|
| CH | 669898 | 4/1989 |
| DE | 1949923 | 4/1971 |

(Continued)

OTHER PUBLICATIONS

McKellop, et al., Development and Clinical Performance of a Reversible Titanium Alloy Femoral Intramedullary Nail, Scientific Exhibit #3512, American Academy of Orthopaedic Surgeons, 58th Annual Meeting, Mar. 7-11, 1991.

(Continued)

*Primary Examiner* — Kevin T Truong
*Assistant Examiner* — Michael Araj
(74) *Attorney, Agent, or Firm* — Fish & Richardson P.C.

(57) ABSTRACT

The present invention relates to a nail and fastener assembly for use in providing a stable construct for optimal fixation of the hindfoot and to methods for implanting the nail and fastener assembly. One embodiment of the nail and fastener assembly provides additional fixation, for example, in the form of one or more threaded bores, to hold the fasteners in a fixed position. Another embodiment provides angled bores to allow multi-planar and multi-axial implantation of the fasteners. In some instances, the fasteners may cross one or more articulating surfaces of the foot. For example, the fastener may traverse one or more of the calcaneo-cuboid and the talo-calcaneal articulating surfaces to aid in more secure stabilization of the hindfoot.

22 Claims, 6 Drawing Sheets

(56) References Cited

U.S. PATENT DOCUMENTS 4,191,185 A 3/1980 Lemieux
4,192,021 A 3/1980 Deibig et al.
4,219,015 A 8/1980 Steinemann
4,279,249 A 7/1981 Vert et al.
4,280,233 A 7/1981 Raab
4,292,694 A 10/1981 Koeneman
4,338,926 A 7/1982 Kummer et al.
4,429,690 A 2/1984 Angelino-Pievani
4,457,301 A 7/1984 Walker
4,465,065 A 8/1984 Gotfried
4,475,545 A 10/1984 Ender
4,503,847 A 3/1985 Mouradian
4,522,202 A 6/1985 Otte et al.
4,523,591 A 6/1985 Kaplan et al.
4,550,449 A 11/1985 Tunc
4,612,923 A 9/1986 Kronenthal
4,622,959 A 11/1986 Marcus
4,644,943 A 2/1987 Thompson et al.
4,655,203 A 4/1987 Tormala et al.
4,705,027 A 11/1987 Klaue
4,733,654 A 3/1988 Marino
4,751,183 A 6/1988 Sonneborn et al.
4,756,307 A 7/1988 Crowninshield
4,776,330 A 10/1988 Chapman et al.
4,781,183 A 11/1988 Casey et al.
4,790,302 A 12/1988 Colwill et al.
4,846,162 A 7/1989 Moehring
4,851,008 A 7/1989 Johnson
4,863,475 A 9/1989 Andersen et al.
4,875,474 A 10/1989 Border
4,875,475 A 10/1989 Comte et al.
4,895,572 A 1/1990 Chernoff
4,896,661 A 1/1990 Bogert et al.
4,898,186 A 2/1990 Ikada et al.
4,911,153 A 3/1990 Border
4,919,666 A 4/1990 Buchhorn et al.
4,943,292 A 7/1990 Foux
4,968,317 A 11/1990 Tormala et al.
4,973,333 A 11/1990 Treharne
4,976,258 A 12/1990 Richter et al.
4,989,186 A 1/1991 Ricker
5,009,664 A 4/1991 Sievers
5,034,013 A 7/1991 Kyle et al.
5,035,697 A 7/1991 Frigg
5,041,114 A 8/1991 Chapman et al.
5,057,110 A 10/1991 Kranz et al.
5,057,111 A 10/1991 Park
5,066,296 A 11/1991 Chapman et al.
5,084,050 A 1/1992 Draenert
5,084,051 A 1/1992 Tormala et al.
5,108,399 A 4/1992 Eitenmuller et al.
5,112,333 A 5/1992 Fixel
5,123,911 A 6/1992 Granger et al.
5,127,913 A 7/1992 Thomas, Jr.
5,190,546 A 3/1993 Jervis
5,201,735 A 4/1993 Chapman et al.
5,236,431 A 8/1993 Gogolewski et al.
5,248,313 A 9/1993 Greene et al.
5,250,049 A 10/1993 Michael
5,263,431 A 11/1993 Wood
5,269,784 A 12/1993 Mast
5,275,601 A 1/1994 Gogolewski et al.
5,292,695 A 3/1994 Galloway
5,413,577 A 5/1995 Pollock
5,441,500 A 8/1995 Seidel et al.
5,458,654 A 10/1995 Tepic
5,472,444 A 12/1995 Huebner et al.
5,484,438 A 1/1996 Pennig
5,501,695 A 3/1996 Anspach et al.
5,514,137 A 5/1996 Coutts
5,520,690 A 5/1996 Errico et al.
5,549,610 A 8/1996 Russell et al.
5,569,250 A 10/1996 Sarver et al.
5,584,836 A 12/1996 Ballintyn et al.
5,603,715 A 2/1997 Kessler
5,618,286 A 4/1997 Brinker
5,653,709 A 8/1997 Frigg
5,658,287 A 8/1997 Hofmann et al.
5,662,472 A 9/1997 Grutzner
5,720,766 A 2/1998 Zang et al.
5,725,541 A 3/1998 Anspach, III et al.
5,730,744 A 3/1998 Justin et al.
5,741,266 A 4/1998 Moran et al.
5,741,282 A 4/1998 Anspach, III et al.
5,743,914 A 4/1998 Skiba
5,766,174 A 6/1998 Perry
5,776,194 A 7/1998 Mikol et al.
5,792,400 A 8/1998 Talja et al.
5,810,821 A 9/1998 Vandewalle
5,836,949 A 11/1998 Campbell, Jr. et al.
5,855,579 A 1/1999 James et al.
5,868,746 A 2/1999 Sarver et al.
5,871,484 A 2/1999 Spievack et al.
5,876,402 A 3/1999 Errico et al.
5,879,389 A 3/1999 Koshino
5,895,390 A 4/1999 Moran et al.
5,927,978 A 7/1999 Muller
5,928,267 A 7/1999 Bonutti et al.
5,935,127 A 8/1999 Border
6,004,323 A 12/1999 Park et al.
6,015,937 A 1/2000 Brånemark
6,019,761 A 2/2000 Gustilo
6,053,918 A 4/2000 Spievack
6,106,528 A 8/2000 Durham et al.
6,120,504 A 9/2000 Brumback et al.
6,123,708 A 9/2000 Kilpela et al.
6,168,595 B1 1/2001 Durham et al.
6,197,029 B1 3/2001 Fujimori et al.
6,228,086 B1 5/2001 Wahl et al.
6,248,108 B1 6/2001 Törmälä et al.
6,261,291 B1 7/2001 Talaber et al.
6,270,304 B1 8/2001 Freedland
6,270,499 B1 8/2001 Leu et al.
6,296,645 B1 10/2001 Hover et al.
6,309,392 B1 10/2001 Alexander et al.
6,319,253 B1 11/2001 Ackeret et al.
6,368,319 B1 4/2002 Schaefer
6,383,187 B2 5/2002 Törmälä et al.
6,443,954 B1 9/2002 Bramlet et al.
6,488,684 B2 12/2002 Sterghos et al.
6,514,253 B1 2/2003 Yao
6,524,314 B1 2/2003 Dean et al.
6,527,775 B1 3/2003 Warburton
6,572,620 B1 6/2003 Schon et al.
6,572,655 B1 6/2003 Johnson
6,579,293 B1 6/2003 Chandran
6,602,255 B1 8/2003 Campbell et al.
6,605,090 B1 8/2003 Trieu et al.
6,626,906 B1 9/2003 Young
6,673,116 B2 1/2004 Reiley
6,706,046 B2 3/2004 Orbay et al.
6,709,436 B1 3/2004 Sturgeon et al.
6,730,093 B2 5/2004 Saint Martin
6,755,834 B2 6/2004 Amis
6,783,529 B2 8/2004 Hover et al.
6,786,908 B2 9/2004 Hover et al.
6,926,720 B2 8/2005 Castaneda
6,951,561 B2 10/2005 Warren et al.
7,655,009 B2 2/2010 Grusin
2001/0021851 A1 9/2001 Eberlein et al.
2001/0031966 A1 10/2001 Tormala et al.
2001/0037112 A1 11/2001 Brace et al.
2002/0029041 A1 3/2002 Hover et al.
2002/0062128 A1 5/2002 Amis
2002/0072748 A1 6/2002 Robioneck
2002/0133156 A1 9/2002 Cole
2002/0133158 A1 9/2002 Saint Martin
2002/0151898 A1 10/2002 Sohngen et al.
2003/0009219 A1 1/2003 Seyr et al.
2003/0018336 A1 1/2003 Vandewalle
2003/0055428 A1 3/2003 Swanson
2003/0069581 A1 4/2003 Stinson et al.
2003/0078583 A1 4/2003 Biedermann et al.
2003/0097131 A1 5/2003 Schon et al.

| | | | |
|---|---|---|---|
| 2003/0195515 | A1 | 10/2003 | Sohngen |
| 2003/0199876 | A1 | 10/2003 | Brace et al. |
| 2004/0030342 | A1 | 2/2004 | Trieu et al. |
| 2004/0092942 | A1 | 5/2004 | Reiley |
| 2004/0097935 | A1 | 5/2004 | Richelsoph et al. |
| 2004/0127899 | A1 | 7/2004 | Konieczynski et al. |
| 2004/0127900 | A1 | 7/2004 | Konieczynski et al. |
| 2004/0127904 | A1 | 7/2004 | Konieczynski et al. |
| 2004/0158252 | A1 | 8/2004 | Prager et al. |
| 2004/0260290 | A1 | 12/2004 | Zander et al. |
| 2005/0101958 | A1 | 5/2005 | Adam |
| 2005/0187550 | A1 | 8/2005 | Grusin |
| 2005/0261555 | A1 | 11/2005 | Guzman et al. |
| 2006/0100623 | A1 | 5/2006 | Pennig |
| 2006/0173457 | A1 | 8/2006 | Tornier |
| 2007/0123878 | A1 | 5/2007 | Shaver et al. |
| 2008/0015587 | A1 | 1/2008 | Munoz |
| 2008/0287949 | A1 | 11/2008 | Keith et al. |

FOREIGN PATENT DOCUMENTS

| | | | |
|---|---|---|---|
| DE | 196 29 011 | A1 | 1/1998 |
| DE | 19629011 | | 1/1998 |
| DE | 19945611 | | 9/2001 |
| DE | 203 00 987 | U1 | 4/2003 |
| DE | 20300987 | | 5/2003 |
| DE | 203 09 399 | U1 | 8/2003 |
| DE | 20309399 | | 10/2003 |
| DE | 19945611 | | 11/2005 |
| EP | 0 299 004 | B1 | 1/1989 |
| EP | 0 355 411 | A1 | 2/1990 |
| EP | 0355411 | | 2/1990 |
| EP | 0 491 983 | A1 | 7/1992 |
| EP | 0 583 442 | B1 | 2/1994 |
| EP | 0299004 | | 3/1994 |
| EP | 0491983 | | 3/1996 |
| EP | 0 710 091 | B2 | 5/1996 |
| EP | 0710091 | | 5/1996 |
| EP | 0583442 | | 10/1996 |
| EP | 1 415 604 | A1 | 5/2004 |
| EP | 1415604 | | 5/2004 |
| FR | 2710835 | | 4/1995 |
| SU | 1692566 | | 11/1991 |
| SU | 1692566 | A1 | 11/1991 |
| WO | WO 96/35387 | | 11/1996 |
| WO | WO 98/41161 | | 9/1998 |
| WO | WO 98/46169 | | 10/1998 |
| WO | WO98/41161 | | 12/1998 |
| WO | WO 00/61018 | | 10/2000 |
| WO | WO00/61018 | | 6/2002 |
| WO | WO 03/017822 | | 3/2003 |

OTHER PUBLICATIONS

Raiha, 'Biodegradable Implants as Intramedullary Nails. A Survey of Recent Studies and an Introduction to Their Use,' Clinical Materials, 10:35-39 (1992).

Hofmann, 'Editorial Biodegradable Implants in Orthopaedic Surgery,' Clinical Materials, 10:1 Table of Contents (1992).

"Alta Modular Trauma System . . . The leading edge in fracture management technology . . . The alta® tibial/humeral rod module for reamed and non-reamed procedures," 10 pages, Jan. 1992.

Kato, et al., The Weakest Link in the Bone Plate Fracture System: Changes with Time, Clinical and Laboratory Performance of Bone Plates, ASTM STP 1217, ed. By Harvey and Games, pp. 85-94, (1994).

Nazre, et al., 'Theoretical Strength Comparison of Bioabsorbable (PLLA) Plates and Conventional Stainless Steel and Titanium Plates Used in Internal Fracture Fixation,' Clinical and Laboratory Performance of Bone Plates, ASTM STP 1217, J.P. Harvey, Jr., and R. F. Games, Eds., American Society for Testing and Materials, Philadelphia, 1994, pp. 53-64.

Yeadon, et al., 'Influence of Axially Flexible Plates on Bone Healing: A Biomedical Study in Canine Femora,' CMBES 20 CCGB Vancouver 1994, pp. 34-35.

Rommens, et al., "Retrograde locked nailing of humeral shaft fractures: A review of 39 patients," J. Bone Joint Surg. Br., 77(4):667, (1995) http://www/ncbi.nlm.nih.gov/entrez/query.fcgi?cmd=Retrieve&db=PubMed&dopt=Abstra . . . .

Biomet, Inc. Brochure 'Unifiex® Surgical Technique,' pp. 1-12, 1995.

Biomet, Inc. Medical Products Brochure, Uniflex® Nailing System, pp. 1-14 (1995).

Biomet, Inc. Medical Products Brochure, Trauma Systems Uniflex™ Tibial Nail System, 4 pages (1995).

Biomet, Inc. Brochure 'Uniflex® Surgical Technique,' pp. 1-16, 1995.

Biomet Inc. Vector Intertrochanteric Nail, Version Two, 19 pages, 1995.

Biomet Inc., Biomet Retrograde Femoral Nail, 6 pages, 1995.

Biomet Inc., Biomet Retrograde Femoral Nail Surgical Technique, 12 pages, 1995.

Biomet Inc., AIM™ Titanium Femoral Nail, 11 pages, 1995.

Biomet, Inc., Vector Intertrochanteric Nail, Version One, 18 pages, 1995.

Biomet Medical Products Inc. 'Interlocking Nail,' 14 pages, 1995.

Ferguson, et al., 'Finite element stress analysis of a hybrid fracture fixation plate,' Med. Eng. Phys., 10(5):241-250, 1996.

Foux, et al., 'Improved Fracture Healing with Less Rigid Plates A Biomedical Study in Dogs,' Clinical Orthopaedics and Related Research, 339:232-245, 1997.

Simon, et al., Bioresorbable Fracture Fixation in Orthopedics: a Comprehensive Review. Part II. Clinical Studies, The American Journal of Orthopedics, pp. 754-762, (Nov. 1997).

Smith & Nephew Brochure entitled "Intramedullary Supracondylar Nail Surgical Technique," by David Seligson, M.D., et al., pp. 1-29 (Mar. 1998).

http://www.biometmerck.com/english/products/tratima/ankle/htm, on page, Jan. 6, 2005,.

Orthofix Retrograde Nailing System, 'The long and the short of it,' Orthofix Always Inovating Brochure, 10 pages, 2002.

Orthofix Operative Technique Brochure entitled 'The Ankle Arthrodesis Nail,' by Profs. Dr. D. Pennig, 16 pages, 2002.

Two sheets of schematic drawings of nail marked as 'Drawing Printed 81006321B,' and one sheet of 'Period Sales Analysis by Planner' showing first sale date of Sep. 2003.

DePuy website paper entitled the VersaNail System: A Versatile Ankle Fusion Option, pp. 1-3 (copyright 2002-2004).

Dr. Rodriguez's www.chicagofootandanklesurgery.com (Ante Fusion) web page, pp. 1-3 (Mar. 11, 2005 http://www.cfaas.corn/anklefusion.htm).

Encore: True/Fix® Proximal Humeral Nail web page, pp. 1-2, Jan. 19, 2005 http://www.encoremed.com/orthopedics/products/trauma/proximal_humeral_nail.html.

EBI Products website paper entitled "Excellence By Innovation" one page (undated), Sep. 2010.

Brochure of Intramedullary Nail. One Nail . . . Diaphyseal Fractures.

URTN System Introduction, The Titanium Unreamed Tibial Nail System: the next generation in Unreamed Tibial Nails from Synthes and the AO/ASIF, one page, Sep. 28, 2010.

Parts List, undated, Sep. 28, 2010.

EBI Products website paper entitled "Excellence By Innovation" one page, May 30, 2012.

Brochure of Intramedullary Nail. One Nail . . . Diaphyseal Fractures, May 30, 2012.

Parts List, undated, May 30, 2012.

URTN System Introduction, The Titanium Unreamed Tibial Nail System: the next generation in Unreamed Tibial Nails from Synthes and the AO/ASIF, one page, May 30, 2012.

Ordway, Craig B., AIM Titanium Femoral Nail System Surgical Technique, Ace Medical Company, pp. 1-8, 1994.

Brochure entitled "Stryker T2™ Proximal Humeral Nailing System Operative Technique" Stryker Trauma®, 20 pages, 2003.

Office Action for U.S. Appl. No. 13/614,006, mailed Mar. 19, 2013.

Office Action for U.S. Appl. No. 13/483,742, mailed Mar. 28, 2013.

HINDFOOT NAIL

Matter enclosed in heavy brackets [ ] appears in the original patent but forms no part of this reissue specification; matter printed in italics indicates the additions made by reissue.

FIELD OF THE INVENTION

The invention relates to nail and fastener assemblies that provide stable fixation of the hindfoot.

BACKGROUND

Serious ankle problems can be caused by a number of conditions, such as arthritis (e.g., osteoarthritis, rheumatoid arthritis), diabetes, trauma, accidents, or severe deformation. One solution is to replace the ankle joint with an implant or ankle prosthesis. However, prostheses often fail due to subsidence, wear, and loosening within a few years following implantation. There are also anatomical considerations that make such implants non-feasible in some cases. Poor results with prostheses have led many surgeons to abandon implant arthroplasty in more serious cases and return to ankle arthrodesis—fusing the joint to ultimately result in bone fusion. Often, by the time fusion is selected as the best option, there is minimal motion at the joint prior to surgery.

Ankle fusion typically involves using screws and pins to hold the bone together. In a typical fusion surgery, the ankle joint is fused, allowing the tibia (shinbone) to grow together or fuse with the talus bone, the bone of the ankle that articulates with the tibia and fibula, and the calcaneus, the bone that forms the ankle joint. A long ankle arthrodesis "nail" may be inserted through the heel and fixed into place with screws or pins. Often, one or more screws or pins are inserted into the calcaneus, the bone at the lower back part of the foot forming the heel, which provides more stability.

Many of the currently available ankle fusion systems are less than optimal. One reason is because the screws or pins used to fuse the foot bones are secured only into the foot bones themselves; they are not secured to the ankle arthrodesis nail through which they are received. In some instances, an unsecured screw or pin can dislodge itself from the patient's bone and migrate out over years of use. Thus, there is a need in the art to provide a better solution to reduce the risk of migration.

Another reason that many of the currently available fusion systems are less than optimal is because they do not have angled fastener-receiving holes that allow for multi-planar fixation. Alternatively, dangled holes are present, they are not provided at optimal angle ranges for securing and immobilizing the ankle.

In some commercially available systems, the center of the fastener-receiving hole opening(s) in the ankle arthrodesis nail is perpendicular to the longitudinal axis of the nail, such that when the fastener is inserted, it is also perpendicular to the nail. This does not allow the surgeon to achieve purchase into preferred bones of the foot, but instead, limits the surgeon to securing the fastener into the calcaneus (the heel bone). Such systems also fail to provide the option of inserting fasteners in multiple axes to provide a more stable fixation system.

Moreover, fusion systems typically include one or more fasteners that engage only one foot bone in use. The fasteners do not cross articulating surfaces. It would be advantageous to provide a system that allows one or more fasteners to cross one or more articulating surfaces of the bones in the foot in order to provide more stability.

Another disadvantage of some fusion systems is that they do not provide nails with reinforced distal portions. If the nail is the same diameter throughout its length, but there are fastener holes in the distal portion, the implant may be weaker at that portion due to increased stresses from the patient's weight. Thus, there is a need for a fusion system that provides greater rigidity and stability in use.

Accordingly, it would be advantageous to provide a nail and fastener assembly that addresses many of the problems that have not been solved by currently-available systems.

SUMMARY

The present invention comprehends various embodiments of nail and fastener assemblies, which may be employed, among other things, for use in providing a stable construct for optimal fixation of the hindfoot. It also comprehends various methods for implanting the nail and fastener assemblies.

Because bone quality is typically poor in patients who are candidates for this procedure, it is beneficial for a system to include a nail that provides additional fixation to hold the fasteners, which may be screws, pins, partially threaded screws, fasteners having a surface with threads or blades of various pitches, shapes, and rotations about the fastener, helical blades, bolts, or any other structure capable of holding and/or engaging bone, in a fixed position. It is also beneficial for a system to provide the option of stabilizing various articulating surfaces of the foot.

Accordingly, certain embodiments of the present invention provide fusion systems with fixation features between the nail and fastener that secure the fastener into the nail. Other embodiments provide a fusion system with one or more openings of the nail that receive fasteners at various angles, allowing one or more fastener to cross one or more articulating surfaces of the foot to provide for multi-planar and multi-axial implantation of the fasteners. Certain structures provide a fusion system with a fastener that crosses one or more of the talo-calcaneal and the calcaneo-cuboid articulating surfaces. Other embodiments combine these features or aspects of them.

One structure according to certain embodiments of the invention includes a hindfoot nail with a threaded fastener-receiving hole. Other structures include angled fastener-receiving bores, and further structures include assemblies adapted to fuse articulating surfaces of a patient's foot. Methods of the invention provide methods for at least partially fusing certain bones of the patient's hindfoot.

Certain devices of the present invention accomplish these results in a number of ways, some of which are discussed in detail below, with reference to the drawings.

DETAILED DESCRIPTION OF THE DRAWINGS

Figure 1:
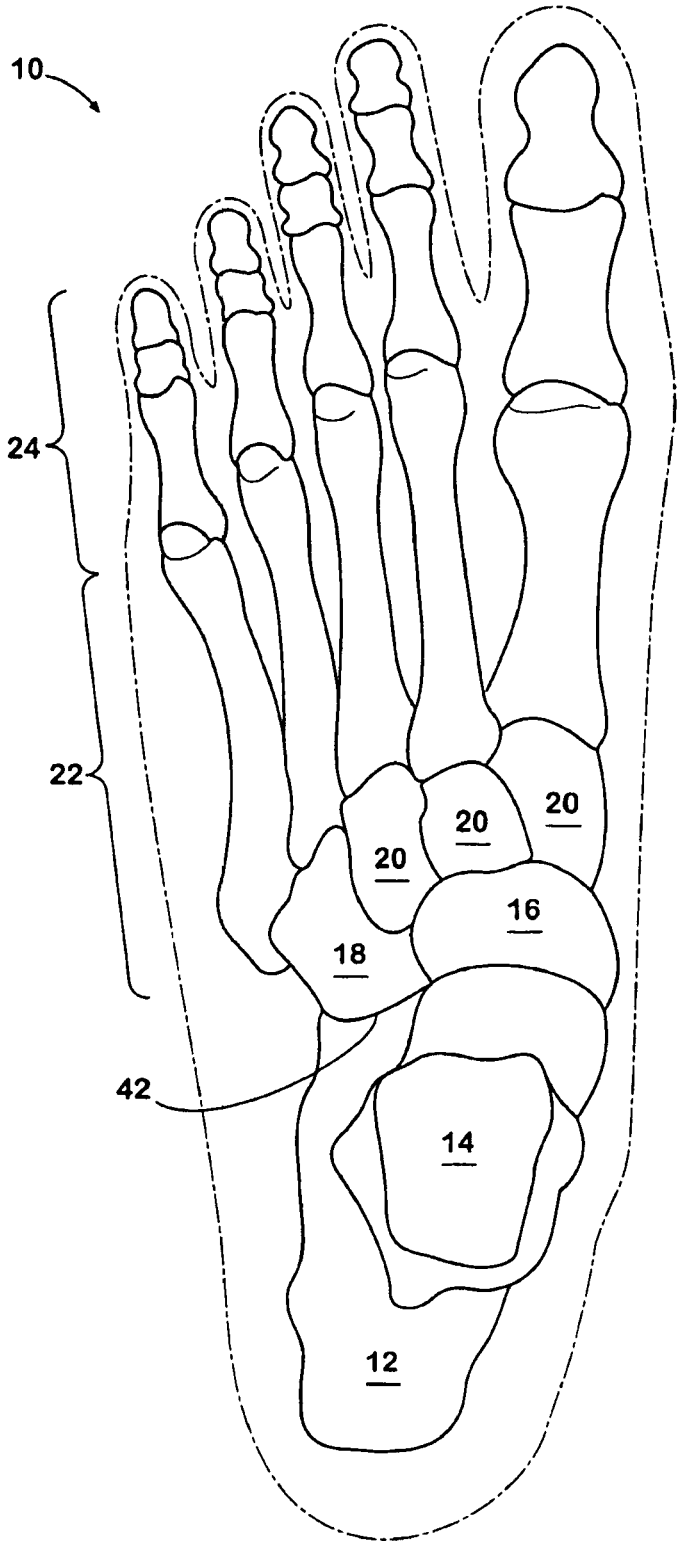
FIG. 1 shows a dorsal view of the anatomy of the foot.
Figure 2:
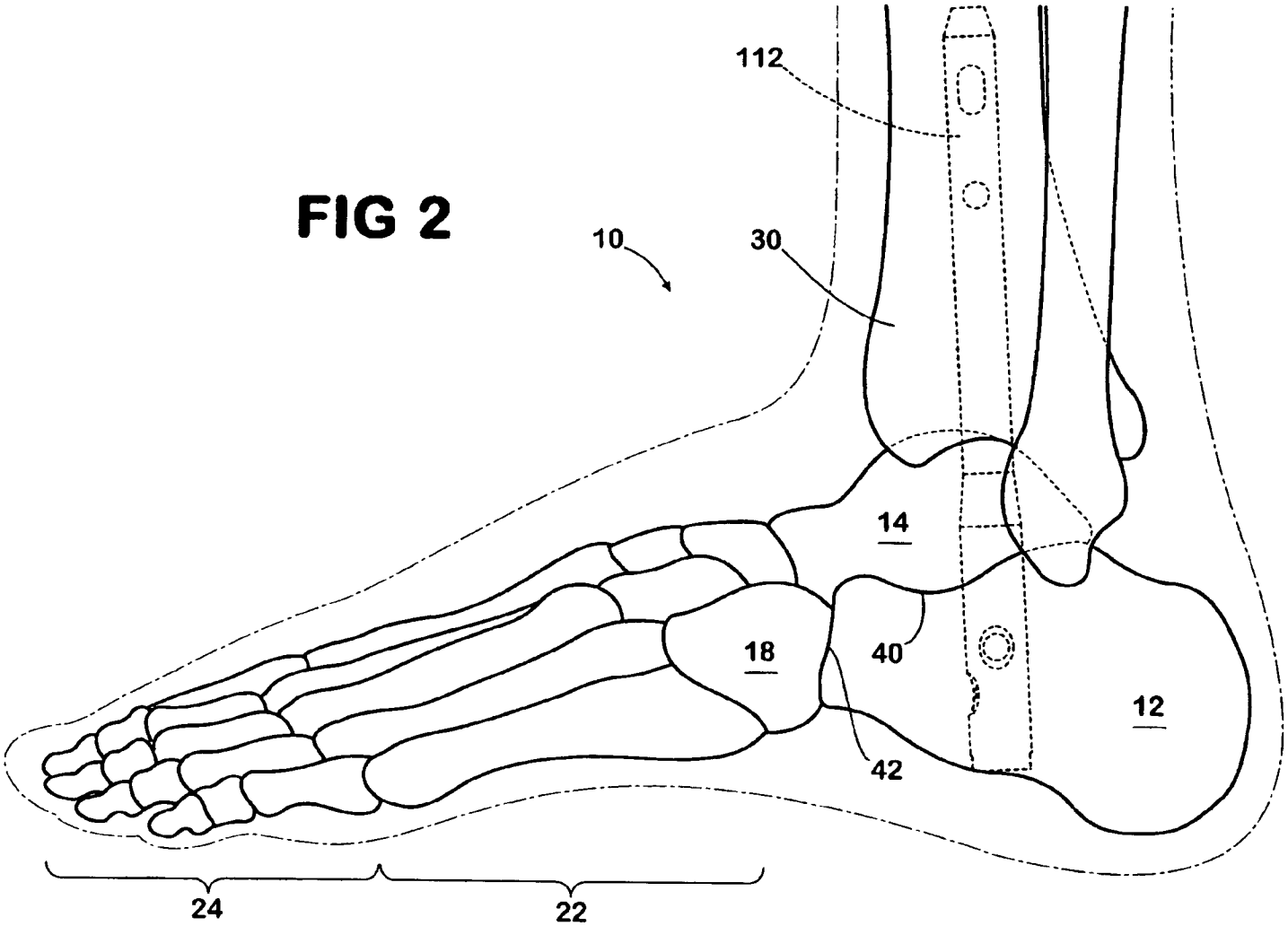
FIG. 2 shows a side view of a foot having an implanted nail according to one embodiment of the invention.

Anatomy of the Foot and Ankle:

There are twenty-six bones in the human foot 10, shown in FIGS. 1 and 2. There are seven tarsal bones: the bone that forms the heel is the calcaneus 12; the talus 14 connects to and supports the tibia 30 (shown in FIG. 2) at the ankle. The five other tarsal bones are the navicular 16, the cuboid 18, and three cuneiforms 20, which form the middle of the foot. Next, five metatarsals 22 form the lower portion of the instep of the foot. The metatarsals 22 radiate out to the phalanges 24, which are the toe bones.

Of the tarsal bones, the talus 14 and the calcaneus 12 are the largest and are adjacent to each other. Also adjacent to the calcaneus 12 is the cuboid 18. The calcaneus 12 and the talus 14 define an articulating surface 40 between the two bones (the talo-calcaneal articulating surface), and the calcaneus 12 and the cuboid 18 also define an articulating surface 42 (the calcaneo-cuboid articulating surface). Some or all of these, or combinations of them, are the foot bones and articulating surfaces that can be of particular interest to certain embodiments of the present invention.

Figure 3:
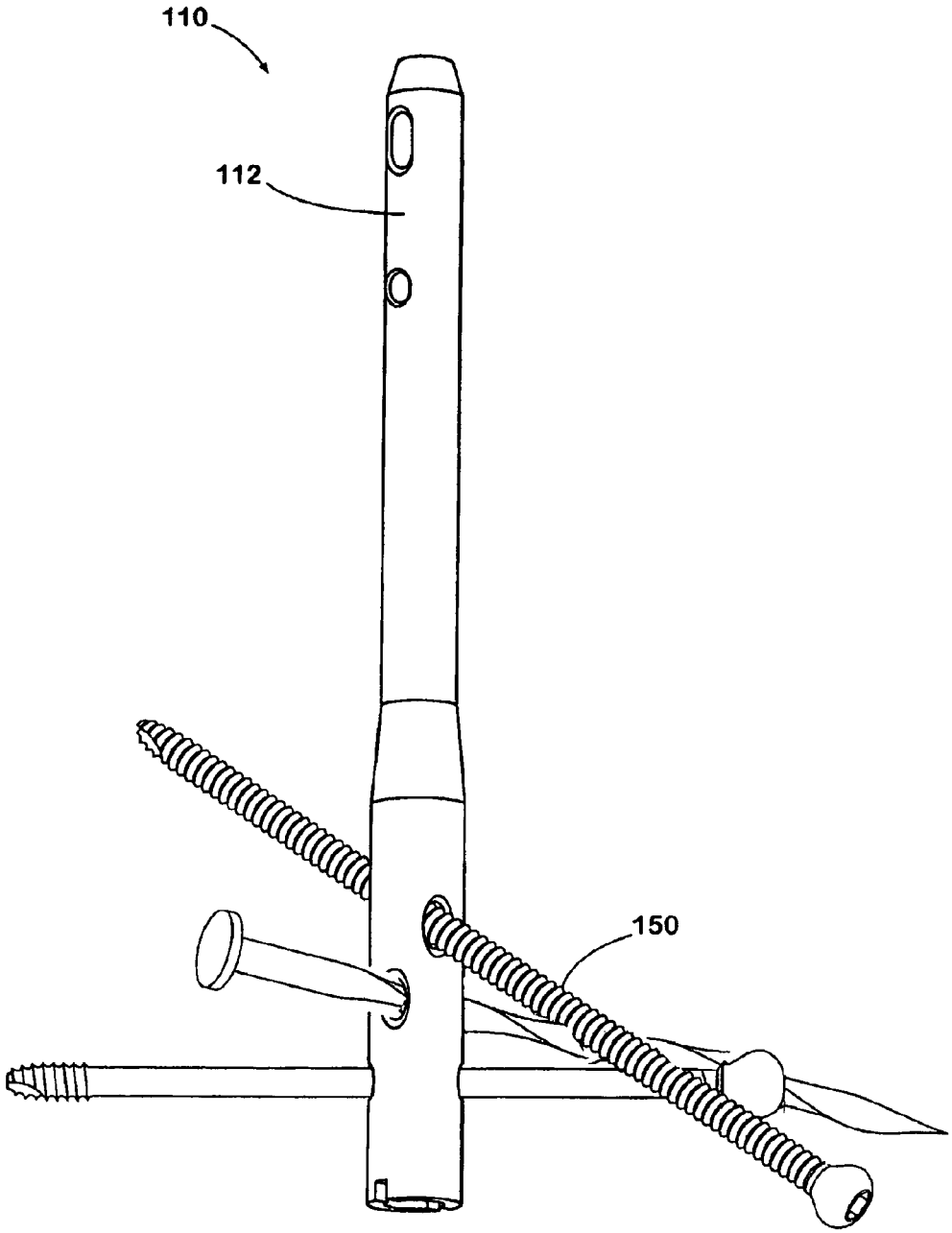
FIG. 3 shows a perspective view of one embodiment of a nail and fastener assembly.
Figure 3A:
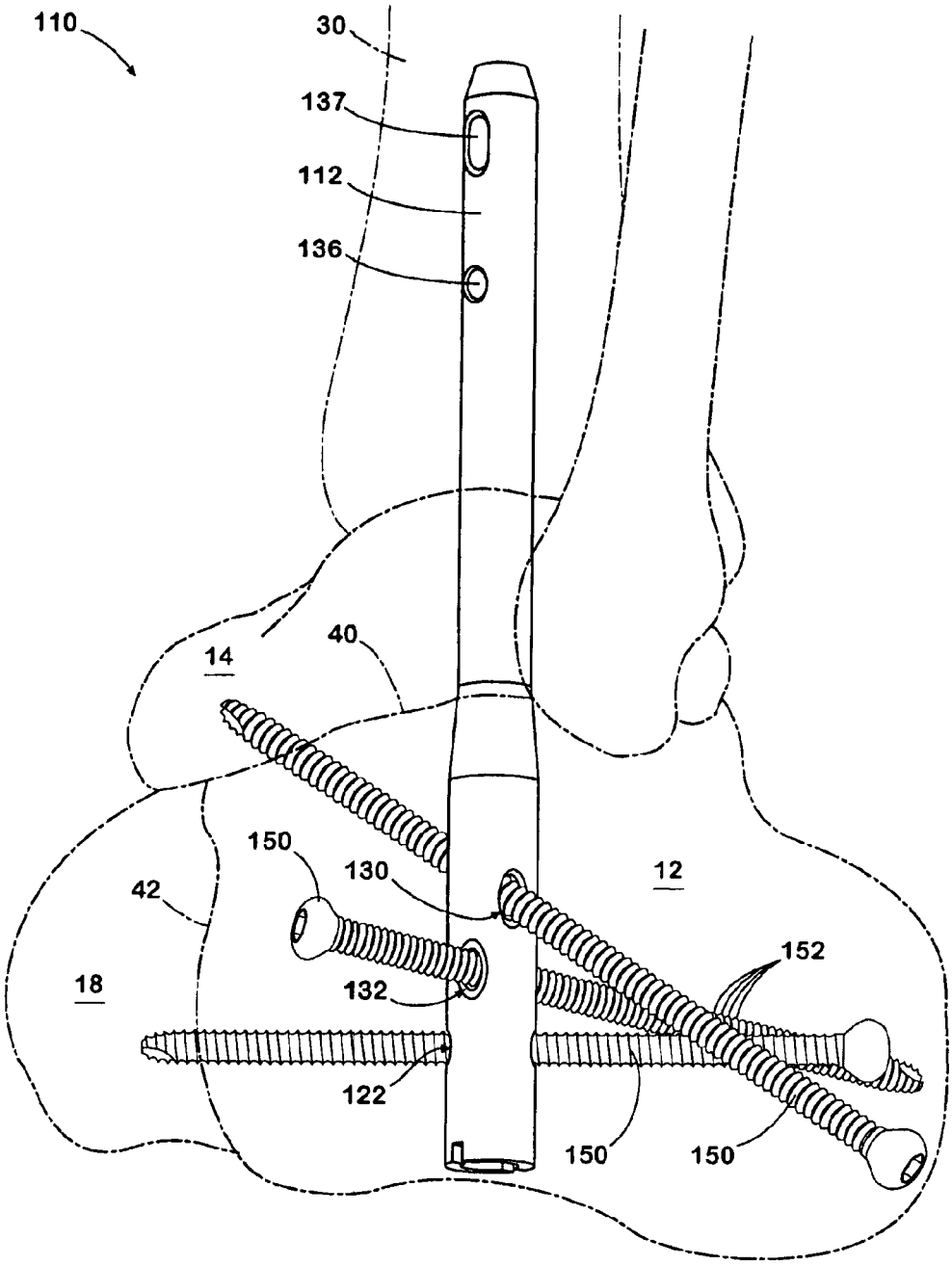
FIG. 3A shows a perspective hind view of a foot having an implanted nail and fastener assembly according to another embodiment of the invention.

Fusion System:

FIGS. 3 and 3A each show a fusion assembly 110 according to embodiments of the invention. Assembly 110 features a nail 112 and one or more fasteners 150. In FIG. 3, some fasteners 150 are shown as partially threaded and partially smooth or fully threaded. In FIG. 3A, all fasteners 150 are shown having threads 152. In short, a surgeon may choose to use a combination of any type of fasteners.

As shown in FIG. 2, nail 112 is adapted to be implanted into a patient's tibial canal. The fasteners 150 are adapted to be inserted through and received by the nail 112 and secure to particular bones of the foot. Different nails 112 are typically provided for the left and right sides of a patient's body to account for differing angles.

Figure 4:
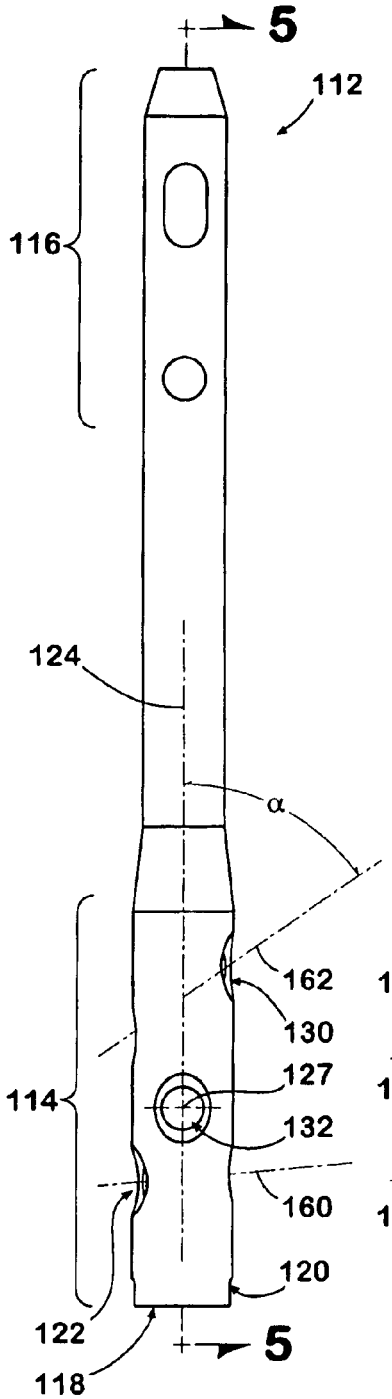
FIG. 4 shows a side view of a nail according to one embodiment of the invention.

As shown in FIG. 4, nail 112 has a distal portion 114 and a proximal portion 116. As best seen in FIGS. 2 and 3A, part of the proximal portion engages the tibia and part of the distal portion engages the calcaneus. Nail 112, as is the case with other components of embodiments disclosed herein, can be formed of Titanium, Titanium alloys, Surgical Steel alloys, or other desired material. Distal portion 114 is shown having a greater outer diameter relative to the proximal portion 116 and may be considered, if desired, also to include a frustoconical transition segment between the portion with the greater outer diameter and the smaller outer diameter. However, distal portion 114 need not necessarily have a greater outer diameter than other portions of the nail 112.

Figure 5:
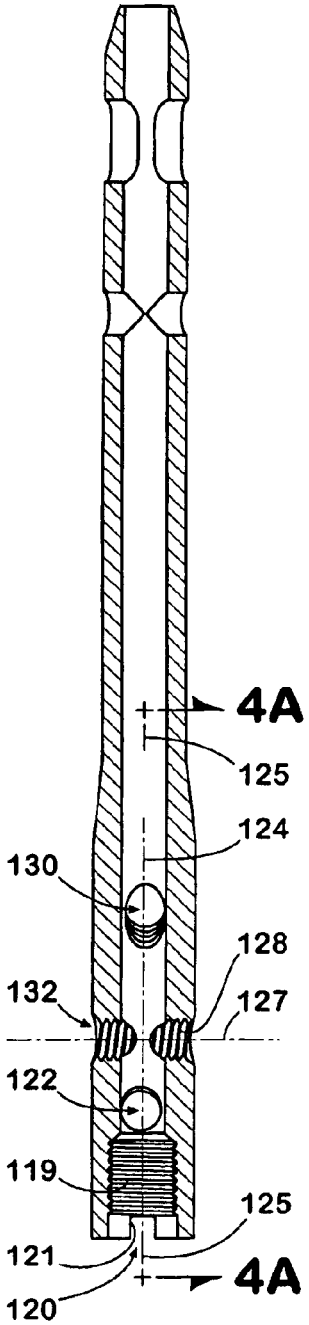
FIG. 5 shows another cross-sectional view of the nail of FIG. 4.

Nail 112 can be also cannulated, if desired. One form of such cannulation is shown in FIGS. 4-5 and can be accomplished by gundrilling or other appropriate techniques. Such cannulation enhances the ability of the nail 112 to be inserted using a closed surgical procedure, such as over a guide wire or rod. Cannulation in the distal portion 114 or portions of it, can be of greater diameter than cannulation in the proximal portion 116 or portions of it, as desired.

At the distal portion 114 is a driving end 118 that has an instrument-receiving portion 120. Instrument-receiving portion 120 may include any type of connecting portion, such as a threaded bore 119 (shown in FIG. 5) that is adapted to receive and fasten to implantation instruments. Instrument-receiving portion 120 may also have an optional keyway 121 (shown in FIG. 6) that can provide additional stabilization with respect to implantation instruments. Other options for connecting the instrument-receiving portion 120 to implantation instruments may be a ball and detent mechanism, a dovetail and slot configuration, a lock and key configuration, or any other stable locking mechanism.

Because distal portion 114 of nail 112 (which again may, if desired, contain some or all of the frustoconical transition shown in FIGS. 4-5) may include one or more angled fastener holes 122, 130, distal portion 114 may be provided with an outer diameter that is larger than the diameter at proximal portion 116. In the particular embodiment shown in FIGS. 4-5, the greater outer diameter can in some ways be considered to provide favorable properties such as any or all of increased resistance to bending, rigidity, strength, stability, durability and enhanced reception and/or retention of fasteners.

One aspect of embodiments of the present invention is that one or more fasteners are received by and secured to a nail, as well as being secured to the patient's bone. See, e.g., FIG. 3A. One structure used to accomplish the securing of the fastener to the nail can be a threaded bore and threaded fastener combination. In this example, the nail can have a threaded bore 128 and the fastener can have corresponding threads 152 at or near the portion received by the nail.

In the specific embodiment shown in FIG. 3A, the fastener is a threaded screw 150. Threads 152 may be provided in any number of shapes (e.g., trapezoidal teeth, triangular teeth, square teeth), pitches, and rotations (e.g., tightly wound around fastener or "loosely" wound such that there is a greater distance between each thread). The screw threads and the threads of the nail need not have the same shape, pitch, or rotation, although they typically will.

In an alternate embodiment (not shown), the fastener is a partially threaded screw. Again, the threads may be provided in any number of shapes, pitches, and rotations. In this example, the threads are preferably located at or near the portion where the threads are secured into nail to prevent their migration.

In a further embodiment, the fastener has a series of cutting edges that engage a patient's bone. Cutting edges may be cutting blades, helical blades, spikes, or any other structure capable of holding and/or engaging bone. Cutting edges may cover all or just a portion of fastener. Alternatively, fastener may feature a bolt, a moly bolt, a tension spring, or any other structure capable of holding and/or engaging bone.

In use, the threaded bore 128 is adapted to receive and secure a corresponding structure on fastener with respect to nail 112, as well as allow fastener to engage with bone. One or more openings in the nail 112 may be provided as threaded bores. It is also possible to provide a nail 112 having a combination of threaded and non-threaded bores (the non-threaded bore structure is described below). It is also possible to provide openings in the nail that are partially threaded and partially non-threaded.

One optional feature that may be provided with assembly 110 is an insert or bushing (not shown) to prevent rotation of the fastener. See pending S&N application Ser. No. 10/999,572, filed Nov. 30, 2004 and titled "Humeral Nail," the entire contents of which are hereby incorporated by this reference. This feature may provide a function similar to fastener anchors that can be used to hang a picture on a wall, i.e., the insert interferes with the rotation of the fastener in the nail and can prevent it from wobbling or threading out, without interfering with the ability of the fastener to insert into the nail at a range of angles. The insert may be used in connection with a threaded or non-threaded bore. It may be secured with respect to nail by the threads, by a rib and locking ring configuration, by injecting a biologic or bone cement through the cannulation as each fastener is inserted, by an interference fit, or any other securing means.

A further aspect of some embodiments of the present invention is that fusion of the hindfoot can be established by connecting and stabilizing certain articulating surfaces of the foot. In one specific embodiment, the talus 14 and the calcaneus 12 are connected to one another by a fastener that crosses the talo-calcaneal articulating surface when implanted. In another specific embodiment, the cuboid 18 and the calcaneus 12 are connected to one another by a fastener that crosses the calcaneo-cuboid articulating surface when implanted. This may be done by specifically targeting these bones using an assembly 110 with angled holes or bores according to one embodiment of the present invention, as shown in FIG. 3A. This particular embodiment provides for multi-planar (and if desired, multi-axial) fixation. The nail may also be adapted to be secured to the tibia 30 for additional stability.

One particularly beneficial aspect of providing angled fastener holes 122, 130 is that they are provided such that any fastener received therein can target specific bones. In one structure according to certain embodiments of the invention, the fasteners are pin-like or substantially smooth. In another structure, the fasteners may have a portion that is threaded (or that contains cutting blades, helically shaped structures having any angle relative to the fastener axis, or other fastening structure to engage bone) that are adapted to secure to a patient's bone, and a portion that is at least partially smooth. These fasteners may be referred to as compression screws, an example of which is shown in FIG. 3.

Compression screws have a portion adapted to attach to a patient's bone, as well as an at least partially smooth portion that articulates with the nail for sliding compression. The at least partially smooth surface is allowed to "slide" within the nail, such that when the patient applies pressure to the implant (for example, if the implant is a weight-bearing implant in the foot, the patient applies pressure when stepping down), the fastener compresses the bones together. The bone fragments are allowed to slide and bear on each other for better healing and fusion of the site.

In certain embodiments, the portion that cooperates with a patient's bone is adapted to cooperate with the calcaneus, and in other embodiments, the portion that cooperates with a patient's bone is adapted to cross one or more articulating surfaces of the foot.

Alternatively, angled fastener holes may have internal threads 128. In use, internal threads 128 of nail 112 cooperate with fastener threads 152 of fasteners 150 to secure the fasteners into the nail 112, as well as into the patient's bone. For ease of reference, fasteners will be referred to as fasteners 150 (which are shown as threaded screws) throughout the remainder of this application, although it is understood that fasteners may take any of the above-described forms, such as compression screws, pins, partially threaded screws, and so forth. See e.g. FIG. 3.

In embodiments in which the fastener is adapted to cross articulating surfaces, fastener holes 122, 130 are provided at optimal angles that allow the surgeon to achieve fastener attachment into particular bones of the foot, such as the calcaneus 12, the talus 14, and the cuboid 18. Angled fastener holes 122, 130 are oriented so that fasteners 150 can be inserted into the nail 112 and cross one or more of the articulating surfaces 40 and 42 of the foot bones.

Figure 4A:
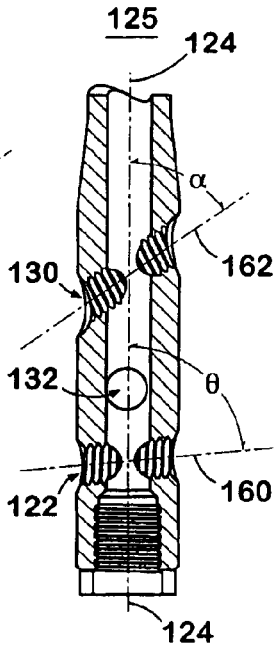
FIG. 4A shows a cross-sectional view of the nail of FIG. 4.

For example, consider nail 112 having a central longitudinal axis 124 as shown in FIGS. 4-5. At least one angled fastener hole 122 is positioned at an angle θ that is between about 45° and about 135° off of the central longitudinal axis 124. (In other words, when a fastener is inserted through the hole 122, the fastener itself creates an axis 160 that forms an angle of between about 45° and about 135° with the central longitudinal axis 124, as shown in FIG. 4A.) In a particular embodiment, at least one angled fastener hole 122 is positioned at an angle between about 65° and about 115° off of the central longitudinal axis 124. In an even more preferred embodiment, the angled fastener hole 122 is positioned at an angle between about 80° and about 90° off of the central longitudinal axis 124, and most preferably, at about 85° off of the central longitudinal axis 124.

Central longitudinal axis 124 also intersects a plurality of planes. One cross-section defined by central longitudinal axis 124 is central plane 125, which is the plane in the page of the paper. This cross-sectional view is shown in FIG. 4A. In addition to its angled orientation with respect to central longitudinal axis 124, angled fastener hole 122 may also be disposed at an angle that is rotated off of the plane 125 of the paper. (In other words, when a fastener is inserted through hole 122, the fastener forms a second plane that is not aligned with plane 125 and would either extend from or retreat into plane 125 of the paper.) In one embodiment, fastener 150 may either be rotated about 0-45° into the plane 125 of the page or rotated about 0-45° out of the plane 125 of the page. In one embodiment, angled fastener hole 122 is rotated about 2-30° off of plane 125. In a further embodiment, it is rotated about 5-15° off of plane 125, and is most preferably, about 10° off of plane 125. (This angle may be in either the medial or the lateral direction.)

In certain embodiments, angled fastener hole 122 is adapted to receive a fastener that targets the cuboid 18 in use, or that at least partially traverses the calcaneo-cuboid articulating surface 42, as shown in FIG. 3.

A second angled fastener hole 130 may also positioned on the distal portion 114 of nail 112. This angled fastener hole 130 may be positioned at an angle α that is between about 25° and about 135° off of the central longitudinal axis 124, such that a fastener inserted therein forms axis 162. In a particular embodiment, second angled fastener hole 130 is positioned at an angle between about 45° and about 115° off of the central longitudinal axis 124. In an even more prefeffed embodiment, second angled fastener hole 130 is positioned at an angle between about 50° and about 75° off of the central longitudinal axis 124, and most preferably, second angled fastener hole 130 is positioned at about 55° off of the central longitudinal axis 124.

Figure 6:
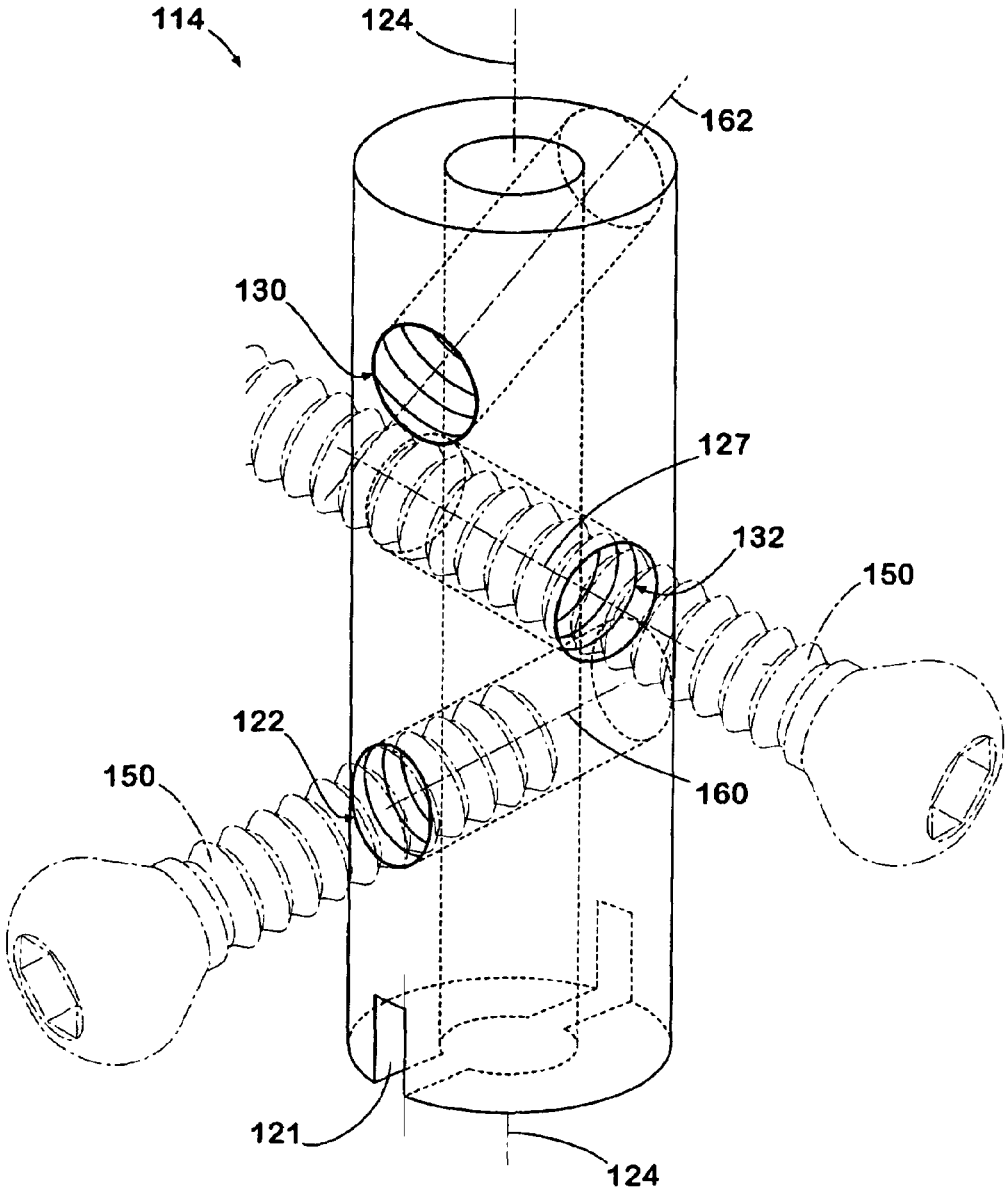
FIG. 6 shows a cross-sectional schematic view of the threaded angled bores of the nail of FIG. 4 showing fasteners (in phantom) inserted.

In addition to its angled orientation with respect to central longitudinal axis 124, second angled fastener hole 130 may also be rotated at an angle off of plane 125. For example, angled fastener hole 130 may be rotated about 0-45° off of plane 125, as shown in FIG. 6. In one embodiment, angled fastener hole 130 is rotated about 2-30° off of plane 125. In a further embodiment, it is rotated about 5-15° off of plane 125, and is most preferably, about 10° off of plane 125. (Again, this angle may also be in either the medial or the lateral direction. It is preferred, although not required, that angled fastener hole 122 be about 10° in the opposite direction of angled fastener hole 130.)

In certain embodiments, second angled fastener hole 130 is adapted to receive a fastener that targets the talus 14 in use, or that at least partially traverses the talo-calcaneal articulating surface 40, as shown in FIG. 3.

There may be provided a third fastener hole 132, which also has internal threads 128, but that may or may not be provided at an angle. Consider nail 112 with a horizontal axis 127 that is perpendicular to the central longitudinal axis 124 and that defines a horizontal plane perpendicular to plane 125 (i.e., extending out from the page). FIG. 5 shows the nail of FIG. 4 cut through a plane that extends perpendicular to plane 125 and then rotated 90° to illustrate the threaded bore of fastener hole 132.

In one embodiment, fastener hole 132 is disposed through distal portion 114 of nail 112 in the horizontal plane, give or take a few degrees. When fastener 150 is inserted through fastener hole 132, the fastener creates an axis that forms an angle of between about 80°-100°, and preferably about 90° with the central longitudinal axis 124, as shown in FIG. 3. In certain embodiments, the third fastener hole 132 is a transverse fastener that targets the calcaneus 12.

In use, a surgeon may choose to use one or more of threaded holes 122, 130, 132, or any combination thereof. For example, a surgeon may only need to use hole 122. In other cases, for example, if more stability is needed, the surgeon will also use 130 and/or hole 132. Alternatively, a surgeon may only use hole 132, but again, may use additional holes for additional stability.

Fasteners 150 may be provided in any number of lengths, although it is preferable that at least one fastener be provided in a length that allows it cross one of more of articulating surfaces 40 and 42. Exemplary fastener lengths may be between 50 to 110 min.

There may also be one or more static locking holes 136 or a dynamic compression slots 137 at the proximal portion 116 of nail 112. These openings 136, 137 are provided for rotational stability of assembly 110 and are typically not threaded or angled, although they can be angled and/or threaded as desired. Although the present inventors believe that it would not be good surgical practice to fix the fasteners to the holes in the proximal portion of nail 112 by threads because the nail 112 should not be overconstrained, it is understood that there could be instances when such fixation would be desired, and threaded upper holes are considered within the scope of this invention.

The surgeon may choose between static or dynamic locking by placing a fastener, pin, or small nail through either a static hole 136 or dynamic slot 137 and into the tibia 30. It is preferred that one of each opening 136, 137 be provided in order to give the surgeon the most flexibility, although this is not required.

Method:

A surgeon first chooses the properly-sized nail 112. (Nails are typically provided in 10-50 cm lengths.) The choice is based on the length of the ankle from the bottom of the calcaneus to a suitable fixation point on the tibia. In essence, the goal is to fuse the nail 112 with the calcaneus 12 and the tibia 30 to immobilize the ankle joint. Typically, the surgeon will remove cartilage from the ankle to encourage the bones to fuse.

Although the surgery may be performed as a closed procedure (i.e., minimally invasive) and it is often preferable for it to be that way due to ease of healing, some surgeons may also wish to remove cartilage from between the bones prior to the procedure, which is often performed using open surgical techniques. In short, embodiments of the invention lend themselves to use during ether type of procedure.

In one embodiment of the procedure, the surgeon makes an incision into the non-weight bearing part of the sole of the foot (i.e., the fatty tissue part of the heel) in line with the tibial planar axis. The surgeon may insert a guide wire into the tibial canal to assist reaming and the placement of nail 112. Once the canal has been reamed to an appropriate diameter and depth, the nail 112 is driven into the center (marrow) portion of the tibia 30, typically using one or more of the instrument-receiving portion 120 or the keyway 121 for securing the implant instrumentation. Preferably, the surgeon uses a C-arm or other image intensifier to insert the nail 112 over a guide wire or rod in a closed surgical procedure as well as to insert the related fasteners.

Instrumentation may also be used to hold and guide drill bits to prepare other bones for receiving fasteners. Similar instrumentation may be used to hold and place a fastener. The fastener can be rotated into place, hammered, or otherwise inserted as desired. In some instances, guide wires may be used to place the fastener as well.

If the surgeon plans to aid the fusion process by inserting a fastener that will cross the calcaneo-cuboid articulating surface 42, the surgeon will insert the fastener through the posterior aspect of the calcaneus, through the opening in the nail, and into the cuboid to target that junction. In the embodiment shown, the surgeon would place fastener 150 into the most inferior angled fastener hole 122. The threads of fastener 150 cooperate with internal threads 128, as well as achieve purchase into the calcaneus 12 and cuboid 18. Alternatively, a compression screw, a pin, an at least partially threaded screw, or other embodiments may be used. In any event, this fastener will typically have a relatively "shallow" angle, being inserted at the calcaneus and at least partially crossing the calcaneo-cuboid articulating surface 42.

Once the first fastener is inserted, the surgeon may gently tap the driving end 118 of the nail 112 to achieve compression of the ankle. If the surgeon plans to place a transverse fastener (in this case, a fastener that will cooperate with the calcaneus 12), the fastener may be inserted through third fastener hole 132 in either the medial to lateral or lateral to medial direction. Even though this fastener is not necessarily strictly horizontal, it tends to be the most horizontally-located of the fasteners.

Next, if the surgeon plans to aid the fusion process by inserting a fastener that will cross the talo-calcaneal articulating surface 40, the surgeon will insert a fastener into the posterior of the calcaneus, through an opening of the nail, and into the talus to target that junction. In the embodiment shown, the surgeon would place fastener 150 into the superior angled fastener hole 130. The threads of fastener 150 will cooperate with internal threads 128, as well as achieve purchase into the calcaneus 12 and talus 14. Alternatively, a compression screw, a pin, an at least partially threaded screw, or other embodiments may be used. In any event, this fastener tends to be the most steeply angled of the three (assuming that all three fasteners are used). Assuming the patient's foot is standing on a horizontal surface, this fastener will have a relatively steep "upward" angle to at least partially cross the talo-calcaneal articulating surface 40.

This procedure has been described as if the surgeon is using three fasteners, although it should be understood that a surgeon may choose to use fewer or more fasteners and that nails according to structures of this invention may also have fewer or more fastener-receiving bores.

After the nail and junction fasteners have been properly placed in the patient's foot, the surgeon will secure the nail 112 with a fastener at the proximal portion 116 of the nail 112. The surgeon may choose between static or dynamic locking by placing the fastener through either a static hole 136 or a dynamic slot 137 in nail 112.

Changes and modifications, additions and deletions may be made to the structures and methods recited above and shown in the drawings without departing from the scope or spirit of the invention and the following claims.

What is claimed is:

1. A method for at least partially fusing a patient's calcaneo-cuboid articulating surface and talo-calcaneal articulating surface in a hindfoot fusion process, the method comprising:

(a) providing a nail having a proximal portion and a distal portion, the distal portion having a first angled fastener-receiving hole and a second angled fastener-receiving hole;

(b) providing a first fastener adapted to be received in the first angled fastener-receiving hole and a second fastener adapted to be received in the second angled fastener-receiving hole;

(c) implanting the nail into a patient's tibial canal;

(d) inserting the first fastener through the first angled fastener-receiving hole in the nail, such that the first fastener at least partially crosses the patient's calcaneo-cuboid articulating surface; and (e) inserting the second fastener through the second angled fastener-receiving hole in the nail, such that the second fastener at least partially crosses the talo-calcaneal articulating surface.

2. The method of claim 1, wherein at least one of the first fastener-receiving hole and the second fastener-receiving hole is at least partially threaded.

3. A method of ankle arthrodesis on a patient, the patient having a tibia, a cuboid, a talus, and a calcaneus, the tibia having a tibial canal, the method comprising the steps of:

a. selecting a properly sized nail;

b. reaming the tibial canal;

c. inserting the nail into the tibial canal;

d. inserting a first fastener into the calcaneus, through the nail, and into the cuboid; and e. inserting a second fastener into the calcaneus, through the nail, and into the talus, wherein a tip portion of the second fastener achieves purchase within the talus.

4. The method of claim 3, further comprising the step of removing cartilage from one or more bones.

5. The method of claim 3, further comprising the step of incising a non-weight bearing part of a sole of the patient's foot.

6. The method of claim 3, further comprising the step of inserting a guide wire into the tibial canal.

7. The method of claim 3, further comprising the step of inserting a transverse fastener into the calcaneus and the nail.

*8. A method for fusing bones in a hindfoot fusion process, comprising:*

*providing a nail having a proximal portion and a distal portion and a central longitudinal axis extending therebetween, the distal portion defining at least two fastener-receiving holes, each of the holes defining a through axis offset and non-perpendicular to the nail axis, the through axes being non-parallel;*

*providing at least two fasteners;*

*implanting the nail into a patient's tibial canal; and*

*inserting one of the fastener through one of the holes in the nail and inserting the other fastener through the other of the holes in the nail, wherein inserting one of the fasteners comprises inserting the one of the fasteners into the talus.*

*9. The method of claim 8 wherein inserting the other fastener comprises inserting the other fastener into the cuboid.*

*10. A method for fusing bones in a hindfoot fusion process, comprising:*

*providing a nail having a proximal portion and a distal portion and a central longitudinal axis extending therebetween, the distal portion defining at least two fastener-receiving holes, each of the holes defining a through axis offset and non-perpendicular to the nail axis, the through axes being non-parallel and constrained to non-parallel planes;*

*providing at least two fasteners;*

*implanting the nail into a patient's tibial canal; and*

*inserting one of the fasteners through one of the holes in the nail and inserting the other fastener through the other of the holes in the nail.*

*11. A method of ankle arthrodesis on a patient, the patient having a tibia, a cuboid, a talus, and a calcaneus, the tibia having a tibial canal, the method comprising:*

*reaming the tibial canal;*

*inserting a nail into the tibial canal;*

*inserting a first fastener into the calcaneus, through the nail, and directed toward the cuboid; and*

*inserting a second fastener into the calcaneus, through the nail, and into the talus, wherein the first and second fasteners are non-parallel and a tip portion of the second fastener terminates within the talus.*

*12. The method of claim 11 further comprising providing the first fastener with sufficient length to engage the cuboid.*

*13. The method of claim 12 wherein inserting the second fastener comprises inserting the second fastener into the cuboid.*

*14. The method of claim 11 further comprising providing the nail with two holes, each for receiving one of the fasteners, the holes having non-parallel through axes.*

*15. The method of claim 14 wherein providing the nail comprises the through axes being constrained to non-parallel planes.*

*16. The method of claim 14 wherein providing the nail comprises the distal portion defining a third hole between the two fastener-receiving holes relative to a central longitudinal axis of the nail.*

*17. The method of claim 16 further comprising providing a third fastener and inserting the third fastener through the third hole in the nail.*

*18. A method for fusing bones in a hindfoot fusion process, comprising:*

*providing a nail having a proximal portion and a distal portion and a central longitudinal axis extending therebetween, the distal portion defining three fastener-receiving holes, at least two of the holes defining through axes offset and non-perpendicular to the nail axis, the third hole being positioned between the at least two of the holes relative to the longitudinal axis;*

*providing three fasteners;*

*implanting the nail into a patient's tibial canal; and*

*inserting the fasteners each through one of the holes in the nail, wherein one of the fasteners is inserted into the talus.*

*19. The method of claim 18 wherein another of the fasteners is inserted into the cuboid.*

*20. A method of ankle arthrodesis on a patient, the patient having a tibia, a cuboid, a talus, and a calcaneus, the tibia having a tibial canal, the method comprising:*

*reaming the tibial canal;*

*inserting a nail into the tibial canal;*

*inserting a first fastener into the calcaneus, through the nail, and directed toward the cuboid;*

*inserting a second fastener into the calcaneus, through the nail, and into the talus, wherein a tip portion of the second fastener terminates within the talus; and*

*inserting a third fastener between the first and second fastener relative to a longitudinal axis of the nail.*

*21. The method of claim 20 further comprising providing the nail with three holes, each hole for receiving one of the fasteners, the holes for receiving the first and second fasteners having non-parallel through axes constrained to non-parallel planes.*

*22. The method of claim 21 wherein providing the nail comprises the third hole being about perpendicular to the nail axis.*

* * * * *